(12) United States Patent
Paden

(10) Patent No.: US 6,227,817 B1
(45) Date of Patent: May 8, 2001

(54) MAGNETICALLY-SUSPENDED CENTRIFUGAL BLOOD PUMP

(75) Inventor: Bradley E. Paden, Santa Barbara, CA (US)

(73) Assignee: Magnetic Moments, LLC, Goleta, CA (US)

( * ) Notice: Subject to any disclaimer, the term of this patent is extended or adjusted under 35 U.S.C. 154(b) by 0 days.

(21) Appl. No.: 09/389,775

(22) Filed: Sep. 3, 1999

(51) Int. Cl.⁷ ..................................................... F04B 17/00
(52) U.S. Cl. ...................... 417/356; 417/365; 417/423.1; 417/423.12
(58) Field of Search ............................ 417/423.12, 423.1, 417/423.14, 423.7, 356, 365

(56) References Cited

U.S. PATENT DOCUMENTS

| | | | |
|---|---|---|---|
| 4,688,998 | * 8/1987 | Olsen et al. | 417/356 |
| 4,763,032 | * 8/1988 | Bramm et al. | 310/90.5 |
| 5,112,202 | * 5/1992 | Oshima et al. | 417/423.7 |
| 5,195,877 | * 3/1993 | Kletschka | 417/356 |
| 5,385,581 | * 1/1995 | Bramm et al. | 623/3 |
| 5,443,503 | * 8/1995 | Yamane | 623/3 |
| 5,470,208 | * 11/1995 | Kletschka | 417/356 |
| 5,695,471 | * 12/1997 | Wampler | 604/131 |
| 5,725,357 | * 3/1998 | Nakazeki et al. | 417/18 |
| 5,840,070 | * 11/1998 | Wampler | 604/131 |
| 5,928,131 | * 7/1999 | Prem | 600/16 |
| 6,015,434 | * 1/2000 | Yamane | 623/3 |

* cited by examiner

*Primary Examiner*—Charles G. Freay
*Assistant Examiner*—Ehud Gartenberg
(74) *Attorney, Agent, or Firm*—Jason S. Crush; Dennis Haszko

(57) ABSTRACT

A magnetically levitated blood pump having a single inlet for accepting blood and tangential volute. The pump includes an impeller formed on a hub that is suspended radially by permanent magnet bearings and axially adjusted via and thrust coil. The hub is rotated by an axial gap permanent magnet DC motor having motor magnets mounted on the hub adjacent to the impeller, a stator formed in the area opposite to the motor magnets, and motor coils formed on the stator. The axial air gap of the motor is formed in the impeller blade path. The motor may have two separate stator members. The current in the thrust coil is controlled by feedback of the impeller axial position measured by sensors. The pump components are compactly configured within a housing.

20 Claims, 3 Drawing Sheets

Virtual Zero Power (VZP) Controller

MAGNETICALLY-SUSPENDED CENTRIFUGAL BLOOD PUMP

BACKGROUND OF THE INVENTION

1. Field of the Invention

The invention relates to blood pumps suitable for permanent implantation in humans. More specifically, it relates to centrifugal pumps with magnetically suspended impellers suitable for use as ventricular assist devices.

2. Description of the Prior Art

Roughly 700,000 patients die from heart disease in the U.S. each year and 35,000 to 70,000 of these could benefit from mechanical circulatory support or a heart transplant. However, only about 2,500 transplant hearts become available each year. This translates to a profound need for a reliable mechanical blood pump to serve as a cardiac assist device or artificial heart.

Several prior-art devices attempt to solve this problem. Indeed, numerous embodiments of blood pumps exist, but are subject to significant operational problems. Such prior-art pumps are discussed hereinbelow.

In U.S. Pat. No. 4,688,998 issued to Olsen et al., a motor stator is disclosed that consists of C-shaped rings. The rings substantially increase the diameter of the pump contrary to the anatomical requirement of small size and weight.

In U.S. Pat. Nos. 4,763,032, 4,994,748, 5,078,741, 5,326,344, and 5,385,581, all issued to Bramm et al., a device is disclosed that requires two inflow channels, which increase the total blood-wetted surface. Among other things, this large contact area between artificial materials and the blood increases immune system response to the pump as well as the probability of thromboembolism. Further, connecting the two inlets of the pump to the heart is complex and requires additional tubing. Thus, anatomical interference of such pumps with natural organs and structures is increased.

In U.S. Pat. No. 5,112,202 issued to Oshima et al., a device is disclosed in the form of a centrifugal pump that utilizes a magnetic coupling with mechanical bearings subject to wear. This pump is not suitable for long-term implantation, as the bearings will eventually fail due to wear.

In U.S. Pat. No. 5,195,877 issued to Kletschka, a device is disclosed that requires two inflow channels, which increase the total blood-wetted surface. This large contact area between artificial materials and the blood increases immune system response to the pump. The large surface area also increases the probability of thromboembolism. Further, connecting the two inlets of the pump to the heart is complex and requires additional tubing. Thus, anatomical interference of the pump with natural organs and structures is increased.

In U.S. Pat. No. 5,443,503 issued to Yamane, a pump device is disclosed that has a jewel bearing. Such bearings are subject to wear in a long-term implant. Further, the jewel bearing is a point of blood stasis and is subject to clotting and may lead to thromboembolism.

In U.S. Pat. No. 5,470,208 issued to Kletschka, a device is disclosed that requires two inflow channels, which increase the total blood-wetted surface. This large contact area between artificial materials and the blood increases immune system response to the pump. The large surface area also increases the probability of thromboembolism. Further, connecting the two inlets of the pump to the heart is complex and requires additional tubing such that anatomical interference of the pump with natural organs and structures is increased. As well, this prior-art device has a point of stasis opposite to the inlet, which is a potential site for thrombus formation.

In U.S. Pat. No. 5,507,629 issued to Jarvik, a device is disclosed that includes a mechanical bearing in the form of a jewel bearing which is a point of blood flow stasis. The blood stasis point is a location of thrombus formation and a source of thromboembolism. Other embodiments of this invention levitate the rotor using only passive magnetic bearings which is inherently unstable especially during the requisite high-speed rotor rotation. Unstable rotors can contact the pump housing and potentially stop the blood flow.

In U.S. Pat. Nos. 5,695,471 and 5,840,070, both issued to Wampler, a blood pump is disclosed. Wampler '471 is similar to the device of Jarvik '629 in that there a stasis point at the jewel bearing. The stasis point is a site of thrombus formation and a source of thromboembolism. Further, the jewel bearing will eventually wear out and the impeller will cease to rotate. Wampler '070 uses a hydrodynamic thrust bearing. Such a bearing is highly inappropriate for use within blood processing because such bearings can damage the blood via high mechanical shear that is inherent to such bearings.

In U.S. Pat. No. 5,725,357 issued to Nakazeki, a device is disclosed in the form of a pump that contains a motor with mechanical bearings subject to wear. Such device is not suitable for a long-term implant as the mechanical bearings will eventually fail and cause the pump to stop working.

In U.S. Pat. No. 5,928,131 issued to Prem, a device is disclosed that uses a radial motor wherein the blood flows through the center of the motor. This reduces the allowable permanent magnet material in the motor and reduces its efficiency. Further, the elongated structure of the pump exposes blood to large regions of foreign material, which increases the likelihood of blood damage and thrombus formation. There is also a large region of high blood shear. Blood shear causes blood damage and can trigger undesirable clotting mechanisms in the body. Finally, the cantilevered design, with both bearings on the inlet side of the impeller impairs the rotor dynamics stability or requires larger, bulkier magnets.

From the discussion above, it becomes critically apparent that existing devices on the market are overly complex, prone to mechanical failure, promote thromboembolism and strokes, and otherwise suffer from shortcomings related to their ineffective designs.

Accordingly, it is desirable to provide for a new and improved, effective rotary blood pump suitable for long-term implantation into humans for artificial circulatory support. What is needed is such a blood pump that is highly reliable. What is also needed is such a blood pump that meets anatomical requirements with a compact physical design. What is further needed is such a blood pump that minimizes blood-wetted surface area. Still, what is needed is such a blood pump that minimizes deleterious effects on blood and its circulatory system, the immune system, and other related biological functions. What is also needed is such a blood pump that is not only resilient to everyday accelerations and bodily movements, but also includes stable rotor dynamics, a high motor efficiency, high fluid efficiency, low power consumption for levitation, low vibration, low manufacturing costs, and increased convenience to the patient. Still further, what is needed is a blood pump which overcomes at least some of the disadvantages of the prior-art while providing new and useful features.

SUMMARY OF THE INVENTION

It is an objective of the present invention to provide a highly reliable rotary blood pump suitable long-term implantation into humans for artificial circulatory support. More specifically, the objects of this invention are: to meet anatomical requirements of a compact device design; minimize blood-wetted surface area; minimize deleterious effects on the blood and the immune system, and other biological functions; be resilient to everyday accelerations and bodily movements; have stable rotor dynamics; have high motor efficiency; have high fluid efficiency; have low power consumption for levitation; have low vibration; have reduced manufacture costs; and have increased convenience to the patient.

The present invention is directed to a magnetically suspended centrifugal blood pump, and includes mixed-flow pumps with an axial inlet and radial outlet. By nature of the novel component configuration of the pump, it is compact and has minimal blood-wetted surfaces. Such compactness reduces internal surface area of the pump so that both impact on the immune system and probability of the formation of blood clots are significantly decreased. Through the use of magnetic levitation, the mechanical shear, and hence damage, to the blood is minimized. Further, high mechanical reliability is achieved due to there being no moving parts that contact one another so as to wear.

The magnetic suspension takes advantage of high-energy magnet technology. Such permanent magnets may be formed of any material such as, but not limited to, neodymium-iron-boron magnets so long as such material has a high coercivity and remanance. These magnets robustly suspend the pump impeller in the blood stream so that it does not impact the housing in normal usage. Such high-energy magnets also provide for high efficiency in an included direct current (DC) brushless motor as well as enable overall compactness of the pump design. Fluid efficiency is achieved by matching the specific speed of the pump to the flow conditions resulting in the centrifugal (i.e., mixed-flow) design concept of the present invention. The pump impeller may be conical or take on any various curved shapes such as are commonly found in water pumps and turbochargers so long as blood damage is avoided. Finally, magnetic levitation provides for low vibration levels in the pump.

Biocompatibility is assured by the present invention due to three important considerations. Such considerations include the operating temperatures, the materials used to fabricate the instant device, and the anatomical fit inherent to the compact design.

High efficiency of the pump results in low temperature rise of the motor. As contact with bodily tissues is inherent to the invention, the reduction in operating temperatures minimizes related damage to surrounding tissues. Exterior materials such as titanium or titanium alloys are used for the outer housing of the invention. Such material surfaces when pure and smooth are relatively inert and aseptic when introduced into the human body so occurrences like immune system rejection and bacterial growth are substantially eliminated. Although titanium is discussed, any similarly suitable material that provides biochemical compatibility with surrounding tissues would be appropriate for use in the present invention. The invention also includes coating of all blood-wetted surfaces by materials such as, but not limited to, diamond-like carbon, titanium nitride, or some form of Teflon® (a non-stick material chemically identified as polytetrafluoroethylene, or PTFE). Such materials promote good blood-flow and provide for good hemocompatiblity. While only a few materials are specifically mentioned hereinabove, it should be understood that equally suitable materials could be utilized without straying from the intended scope of the present invention.

A good anatomical fit is assured through the compactness of the present invention's design. The existence of a single inlet with extreme placement of permanent magnet bearings and motor location within the bladed areas results in a compact configuration. Such compactness in design provides for an anatomical fit suitable for abdominal placement without crowding of body tissues and organs. This is a critical point in that an increase in compactness will reduce the stresses placed on the implant patient and result in a less obtrusive and more comfortable implant. The ultimate result being a decrease in recovery time and an overall increase in device effectiveness.

The invention will be described for the purposes of illustration only in connection with certain embodiments; however, it is to be understood that other objects and advantages of the present invention will be made apparent by the following description of the drawings according to the present invention. While a preferred embodiment is disclosed, this is not intended to be limiting. Rather, the general principles set forth herein are considered to be merely illustrative of the scope of the present invention and it is to be further understood that numerous changes may be made without straying from the scope of the present invention.

BRIEF DESCRIPTION OF THE DRAWINGS

FIG. 1b is a front view of the magnet polarizations for the magnets in the impeller of the pump of FIG. 1a.

DETAILED DESCRIPTION OF THE PREFERRED EMBODIMENTS

The present invention is drawn to a magnetically levitated, axially controlled blood pump. Although this preferred design and use is discussed in detail herein, it should be noted that the present invention may be utilized in a variety of similar manners. Such various settings include, without limitation, chemical flow control, gas flow control including turbine designs, and any situation where a reliable and efficient movement of a fluid substance within a limited space is desired. For purposes of illustration, discussion of the present invention will be made in reference to its utility as a cardiac assist blood pump. Additionally, wiring for power and sensor control has been omitted in the detailed description for the sake of clarity. However, it should be readily understood that such wiring may be accomplished by any known method available to one of ordinary electromechanical skill.

Figure 1A:
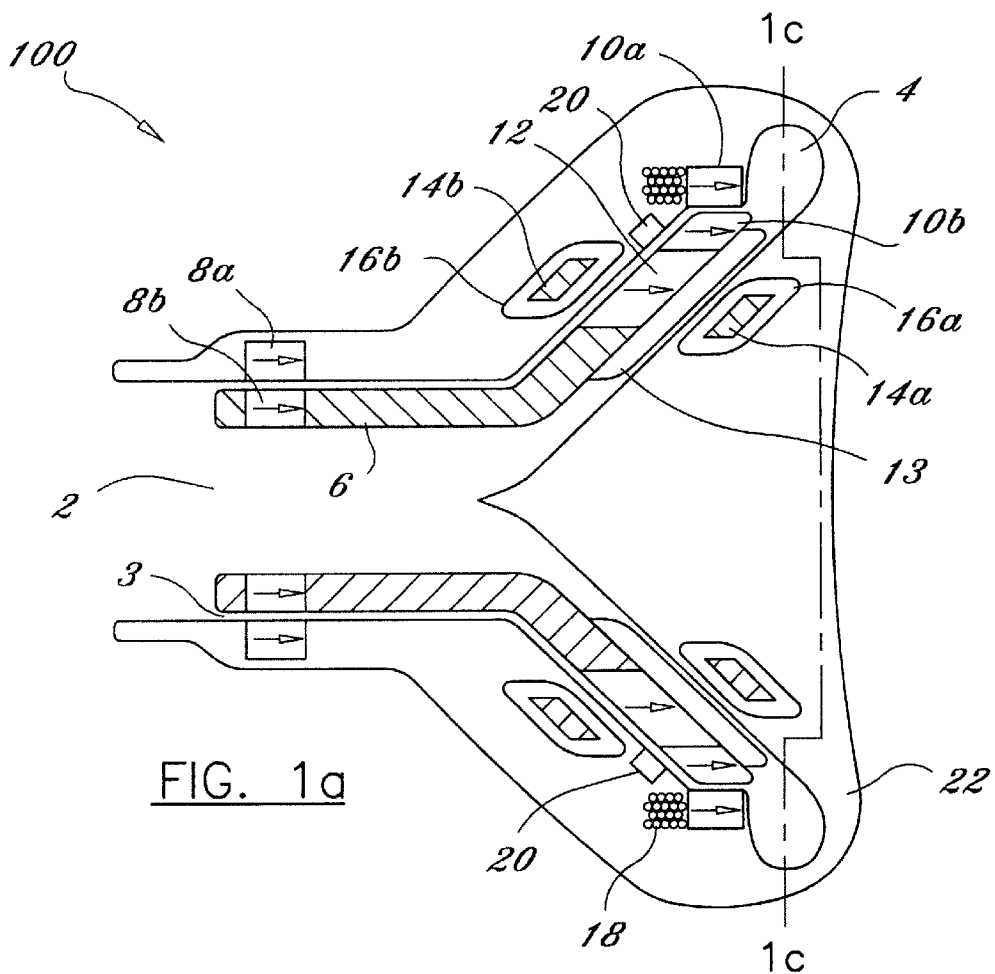
FIG. 1a is a cross sectional view of a first embodiment according to the present invention including a radial bearing at an extreme axial position of an impeller.

Referring now to FIG. 1a, there is shown a preferred embodiment of the cardiac assist blood pump 100. The pump 100 is intended to be fully implanted in an animal or human patient. The pump 100 includes two independent subassemblies in the form of a housing 22 and an rotor hub 6. The pump also includes an inlet 2 and an outlet in the form of a volute 4. For purposes of descriptive clarity, the end of the pump 100 that is opposite the inlet 2 will be referred to as the "rear" of the pump 100. The rotor hub 6 is inertially balanced in a manner consistent with common practice in rotating machinery. The rotor hub 6 is supported magnetically and without contact in a radial direction by permanent magnet (PM) bearings (8a, 8b) and (10a, 10b) and in an axial direction by thrust coil 18. Each of the PM bearings (8a, 8b) and (10a, 10b) consists of an outer race 8a and 10a and an inner race 8b and 10b with magnetization directions shown with arrows. While each of the outer races 8a and 10a and inner races 8b and 10b may be formed from single magnet rings, it should be understood that any common method might be used so long as a PM bearing is formed. For example, magnet ring stacks may be used for the inner and outer races, and ferromagnetic rings serving as pole pieces may be combined with magnet rings.

The PM bearing inner race 10b also interacts with thrust coil 18 to form an active magnetic thrust bearing that actuates axial movement of the rotor hub 6. The thrust coil 18 is disposed toward the outside diameter of one of two stators (14a, 16a) and (14b, 16b). The two stators (14a, 16a) and (14b, 16b) interact with motor magnets 12 to form a four-pole DC brushless motor. The motor magnets 12 are located on the rotor hub 6 alongside impeller blades 13. Such placement of the motor allows a small motor fluid gap to exist due to the increased velocity of blood therethrough. Because of the increased flow of blood in this area, the path need not be wide. Reducing the size of this path—i.e., the motor gap—results in a lighter, more efficient motor structure.

The two stators (14a, 16a) and (14b, 16b) consist of ferromagnetic rings 14a and 14b and motor windings 16a and 16b. The ferromagnetic rings 14a and 14b are preferably composed of laminated 3% silicon-iron, 50% cobalt-iron, 49% nickel iron for example, or any other ferromagnetic materials with high saturation flux density, low bulk conductivity, and low hysteresis. Selective energization of the motor windings 16a and 16b provides forces that interact with motor magnets 12 in a manner consistent with known motor technology so as to rotate the rotor hub 6 and attached impeller blades 13. For a three-phase, four-pole motor, motor windings 16a and 16b consist of twelve individual coils. By utilizing this axial gap motor design having two stators, the overall efficiency is increased while physical size is minimized. Control of such an axial gap motor can be by any known method in the electrical art. However, the preferred controller is the back-EMF type of controller used in most computer disk drives manufactured at present.

Figure 1B:
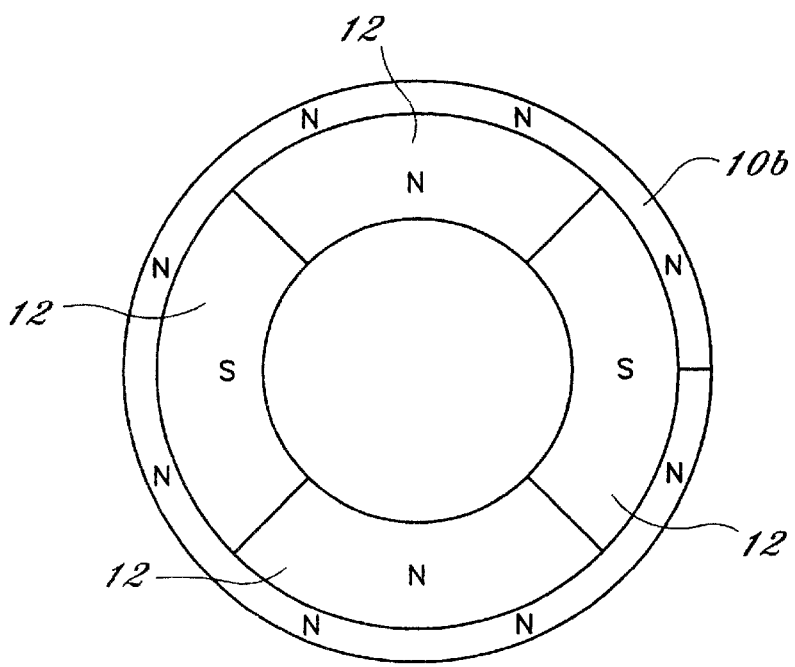

With reference to FIG. 1 b, the motor magnets 12 and PM radial bearing inner race 10b are shown in cross-section where "N" indicates a magnetic North pole and "S" indicating a magnetic South pole. While the inner race 10b has uniform polarity, the motor magnet 12 as shown includes four motor magnets having alternating polarity making a four-pole motor. It should be understood that any number of poles as well as Halbach arrays may be for the motor permanent magnet structure comprising the magnets 12. Moreover, the PM bearings (8a, 8b), (10a, 10b) and motor magnet 12 are designed so that magnetic forces do not cause vibrational forces on the rotor during operation. This is accomplished by precisely forming the PM bearings (8a, 8b) and (10a, 10b) and motor magnet 12 from a magnetic material with high uniformity in addition to high-energy density. Accordingly, all included permanent magnet materials are preferably neodymium-iron-boron or samarium cobalt, but may be selected from any other permanent magnet material so long as they are have high-energy density exhibiting high coercively and remanance.

Figure 1C:
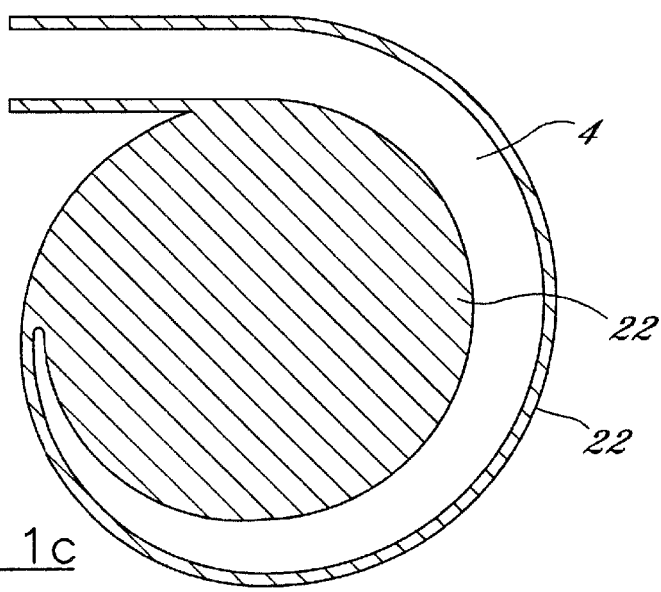
FIG. 1c is a section of the pump volute as shown in FIG. 1a and taken along line 1c—1c.

With additional reference to FIG. 1c, the volute 4 is shown as taken along line 1c—1c FIG. 1a. During operation of the pump 100, blood flowing into the inlet 2 is propelled through the pump 100 by the impeller blades 13 and out of the pump 100 through the volute 4. Through experimentation with existing pump designs, computer simulation called computational fluid dynamics (CFD), and testing with transparent fluid having dispersed particles, the shape of the rotor hub 6, impeller blades 13, and volute 4 can be optimized. The particles enable the visualization of fluid flow in the pump through common means collectively known as "flow visualization." Eddy flows and stagnant flow zones are minimized, and overall pump efficiency is optimized through such methods. Accordingly, the shapes of the rotor hub 6, impeller blades 13, and volute 4 may be adjusted to this end and will vary according to nominal pump speed and flow rates.

Figure 2:
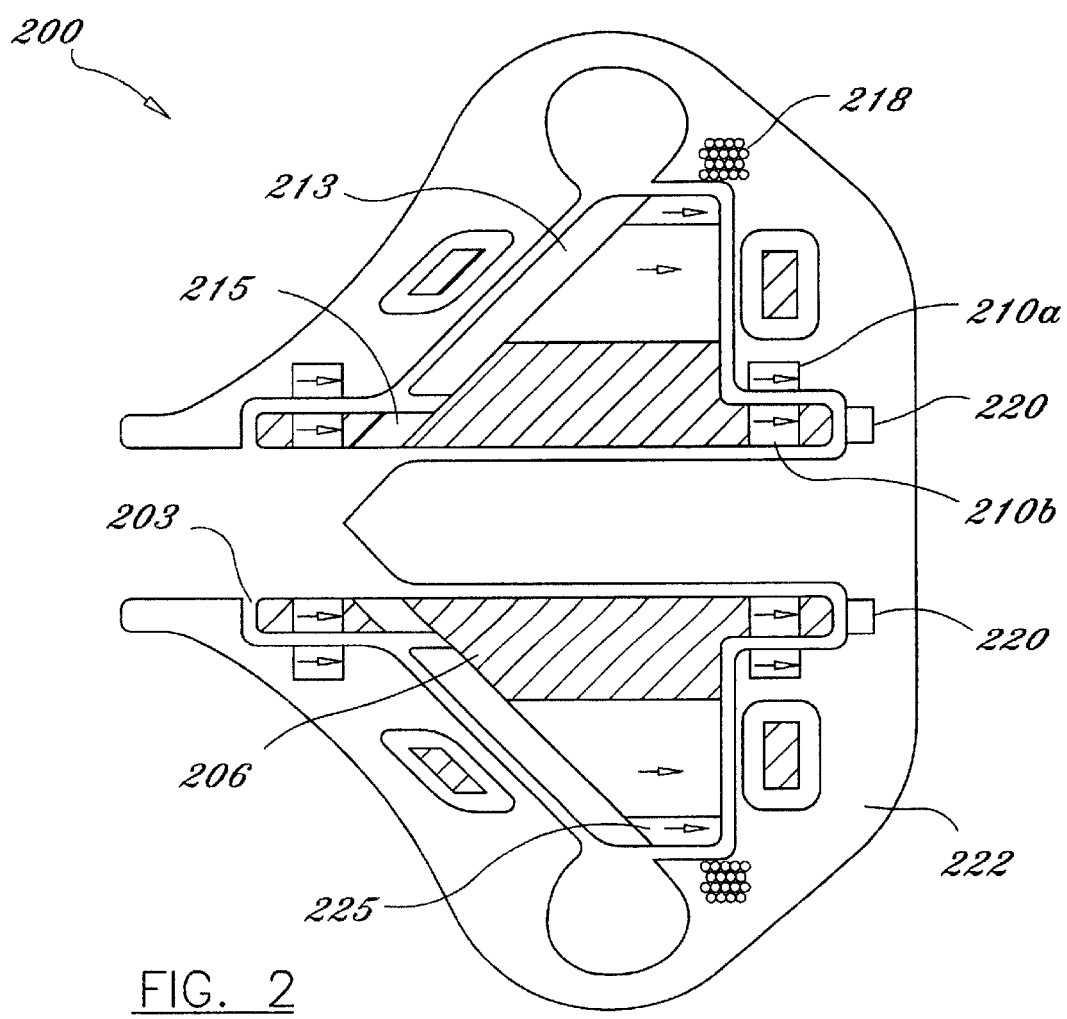
FIG. 2 is a cross sectional view of a second embodiment according to the present invention including a radial bearing at the extreme rear end (away from the inlet) of the pump.

With reference to FIG. 2, a second preferred embodiment of the present invention is shown. Blood pump 200 differs from that of FIG. 1a in that the rear-most PM radial bearings 210a, 210b are relocated and are smaller in diameter. Such a diameter in the rear-most PM radial bearings 210a, 210b has been found to increase overall stability with regard to pitch and yaw motion of the rotor hub 206. Further, relative to FIG. 1a this embodiment differs in that the impeller blades 213 are moved to the inlet side of the rotor hub 206. As well, blood ducts 215 in the rotor hub 206 are added so as to channel blood quickly and directly therethrough. A separate magnet ring 225 is used in conjunction with thrust coil 218 for forming the active magnetic thrust bearing that actuates axial movements. While such an active magnetic thrust bearing arrangement may be formed from as shown by a single coil interacting with a single magnet ring, it should be understood that any common method might be used so long as an active magnetic thrust bearing is formed.

Figure 3:
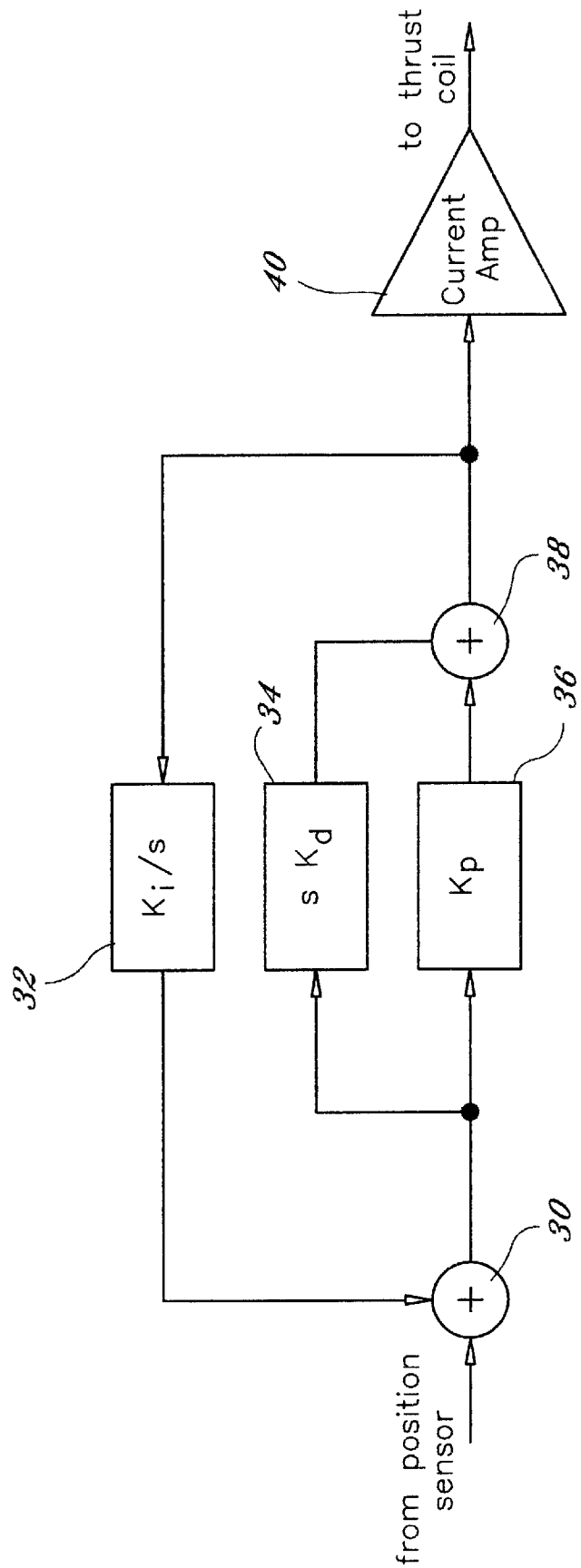
FIG. 3 is a block diagram of a preferred embodiment of a VZP controller.

Common to both embodiments of the present invention as shown in FIGS. 1a–2, the current in thrust coil 18 (218) is controlled as follows. Axial position sensors 20 (220) measure the axial position of rotor hub 6 (206). An external feedback controller (as depicted in FIG. 3) applies current through electrical wiring (not shown) to the thrust coil 18 (218). The current is adjusted in order to position the rotor hub 6 (206) axially without mechanical contact with the housing 2 (222). While virtual zero power (VZP) control is depicted in FIG. 3, it should be understood that there are many possible feedback control algorithms for controlling the coil current. Such algorithms include proportional-integralderivative (PID) or any suitable method well known to those skilled in the art of magnetic bearing control. The axial position sensors 20 (220) can be any reliable non-contact position sensor suitable for unobtrusive placement within the housing 2 (222)—e.g., eddy-current type, variable reluctance type, acoustic, infrared reflectance type, and similar sensors.

With further reference to FIG. 3, one form of a VZP control algorithm is shown in a block diagram. Standard control system design notation is used with "s" being the Laplace variable. The controller consists of an input summing junction 30, an output summing junction 38, integrator block 32, differentiator block 34, proportional gain block 36, and a current amplifier 40. Together, the blocks 32, 34, and 36 impose a coil current in thrust coil 18 (218) in response to the output of the position sensor 20, (220) through a computation depicted in the block diagram. The computation may be made with analog circuits or with digital circuits. The essential features of the VZP controller are that it has low gain at low frequencies—e.g., zero gain at DC is commonly used—and it stabilizes the position of the rotor hub 6 (206) in the axial direction through choice of controller gains $K_i$, $K_p$, and $K_d$.

The control algorithm embodiment shown in FIG. 3 accomplishes low gain at low frequency by way of negative integrator feedback through integrator block 32 of the coil current command input to the current amplifier 40. If the current command is positive, the integrator block 32 increases its output, which is subtracted from the sensor position signal output at 40. The net effect is that the coil current is returned to zero in the steady state, and the rotor hub 6 (206) is moved to a natural axial equilibrium point. The natural equilibrium balances the magnetic negative stiffness forces of the PM bearings with the fluid forces pushing on the impeller blades 13 (213) and rotor hub 6 (206). It should be realized that there are many ways to accomplish VZP control. Accordingly, those skilled in the art may use Linear Quadratic Regulator controllers (LQR) or H-infinity controllers for example, so long as low gain at low frequencies is accomplished and the rotor hub 6 (206) position is stabilized.

During rotational operation of the instant invention, the gap 3 (203) is maintained at a positive value by the magnetic bearings. Blood flows through this gap 3 (203) depending on the details of the design. The direction of blood flow within the gap 3 (203) may be further controlled by adding rifling or small blades on the rotor hub in the gap 3 (203). As well, pressure differentials from one end of the gap 3 (203) to the other can be used to control the flow direction. In all situations, a nonzero flow rate is accomplished and stagnation of blood in gap 3 (203) is avoided. The dimension of gap 3 (203) is designed so as to balance possible blood damage against PM bearing effectiveness. That is to say, blood damage is avoided by keeping the gap sufficiently large, but not so large that the PM bearings lose their effectiveness. Further, the gap 3 (203) can be varied along the length of the pump 100 (200) so that it is small near the PM bearings to achieve good bearing stiffness. Likewise, the gap 3 (203) can be larger in areas where there are no magnetic components and thus reduce average blood shear in the gap 3 (203).

All blood-contacting surfaces of the pump 100 (200) are preferably formed from a blood compatible material such as polished titanium or titanium alloy (e.g., $Ti_6Al_4V)_1$ diamond-like carbon, titanium nitride, or a fluorinated hydrocarbon such as Teflon® (a non-stick material chemically identified as polytetrafluoroethylene, or PTFE). It should be clear that any coating having a high blood compatibility as adjudged by such tests as defined in the International Standards Organization (ISO) document 10993-4 may be used. All included permanent magnet materials are preferably neodymium-iron-boron or samarium cobalt, or any other permanent magnet material with a high-energy density. The ferromagnetic rings 14a and 14b are composed of laminated 3% silicon-iron, 50% cobalt-iron, 49% nickel iron for example, or any other ferromagnetic materials with high saturation flux density, low bulk conductivity, and low hysteresis.

Accordingly, the configuration disclosed above and claimed hereinbelow reveals a compact design having a single inlet that provides for superior anatomical fit. Combining the motor with the impeller near the impeller blades minimizes blood-wetted area. Co-location of the motor with the impeller blades also increases efficiency as the blood gap at the impeller blades is relatively small compared to other parts of the pump. Such a reduced gap results in higher magnetic fields and efficiency in the motor. Through the use of high-energy density magnetic materials and feedback control, the present invention is robust to everyday accelerations. The feedback control of the axial position with the active thrust bearing provides for stable rotor dynamics as does inertial balance of the rotor hub. High fluid efficiency is achieved by using the mixed-flow design and CFD optimization of the pump. Low levitation power is accomplished with the preferred VZP control algorithm that adjusts the rotor position to a point of axial equilibrium so that that no steady-state current is required in the coils during operation. Low vibration is accomplished through inertial balancing of the rotor and control of magnet uniformity and size in the motor and bearings.

It should be understood that the preferred embodiments mentioned here are merely illustrative of the present invention. Numerous variations in design and use of the present invention may be contemplated in view of the following claims without straying from the intended scope and field of the invention herein disclosed.

I claim:

1. A magnetically-suspended centrifugal pump comprising:
    a) a housing including an inlet, a volute, and a flow path between said inlet and said volute;
    b) a hub rotatably disposed within said housing, said hub including a first end and a second end and a hollow cavity between said first end and said second end;
    c) a first permanent magnet bearing located at said first end of said hub and a second permanent magnet bearing located at said second end of said hub;
    d) a plurality of impeller blades located within said flow path and between said first end of said hub and said second end of said hub;
    e) a motor having a circumferential rotor and a circumferential stator, located adjacent to said plurality of impeller blades;
    f) a sensor sensing an axial position of said hub; and
    g) a thrust coil for adjusting said axial position of said hub;
    wherein said first and second permanent magnet bearings passively, radially suspend said hub, said sensor is used to control activation of said thrust coil to maintain said axial position of said hub, and said motor rotates said hub to provide fluid flow through said flow path via said plurality of impeller blades.

2. The pump as claimed in claim 1 wherein said motor is an axial-gap, direct current, brushless motor and said hub includes a motor magnet located within said hub and adjacent to said plurality of impeller blades.

3. The pump as claimed in claim 2 wherein said motor includes a stator means arranged within said housing and located adjacent to said motor magnet.

4. The pump as claimed in claim 3 wherein said stator means includes at least two stators arranged within said housing and on opposite sides of said hub.

5. The pump as claimed in claim 4 wherein each said first and second permanent magnet bearing means includes an inner race located within said hub and an outer race located within said housing, each said inner and outer races being formed by a permanent magnet ring.

6. The pump as claimed in claim 5 wherein said thrust coil is disposed toward an outside diameter of said motor.

7. The pump as claimed in claim 6 wherein said thrust coil and said inner race of said second permanent magnet bearing means form an active magnetic thrust bearing.

8. The pump as claimed in claim 6 wherein said hub further includes a magnet ring located at an outermost radial position on said hub, said thrust coil and said magnet ring forming an active magnetic thrust bearing.

9. The pump as claimed in claim 8 wherein said hub further includes ducts located between said first permanent magnet bearing means and said plurality of impeller blades such that said flow path goes through said ducts.

10. A magneticaly-suspended centrifugal pump comprising:
    a) a housing including an inlet, a volute, and a flow path between said inlet and said volute;
    b) a hub rotatably disposed within said housing, said hub having an axis of rotation and including a substantially hollow cavity arranged along said axis of rotation;
    c) a first permanent magnet bearing having inner and outer races and a second permanent magnet bearing having inner and outer races, each said permanent magnetic bearing located at an opposite extreme location along said axis of rotation;
    d) an impeller disposed upon said hub within said flow path;
    e) a motor having a circumferential rotor and a circumferential stator, located axially adjacent to said impeller;
    f) a sensor sensing an axial position of said hub; and
    g) a thrust coil for adjusting said axial position of said hub;
    wherein said first and second permanent magnet bearings passively, radially suspend said hub, said sensor controls activation of said thrust coil to maintain said axial position of said hub, and said motor rotates said hub to provide fluid flow through said flow path via said impeller.

11. The pump as claimed in claim 10 wherein said motor is an axial-gap, direct current, brushless motor that includes a motor magnet located within said hub and a stator means located within said housing, said impeller being located axially between said motor magnet and said stator means.

12. The pump as claimed in claim 11 wherein said stator means includes at least two stators arranged within said housing and on opposite sides of said hub.

13. The pump as claimed in claim 12 wherein each said inner and outer races of each said first and second permanent magnet bearings are rings of permanent magnet material, and said thrust coil is disposed toward an outside diameter of said motor.

14. The pump as claimed in claim 13 wherein said thrust coil and said inner race of said second permanent magnet bearing form an active magnetic thrust bearing.

15. The pump as claimed in claim 13 wherein said hub further includes a magnet ring located at an outermost radial position on said hub, said thrust coil and said magnet ring forming an active magnetic thrust bearing.

16. The pump as claimed in claim 15 wherein said hub further includes ducts located between said first permanent magnet bearing and said impeller such that said flow path goes through said ducts.

17. A magnetically-suspended centrifugal pump comprising:
    a) a housing including an inlet, a volute, a flow path between said inlet and said volute, and at least two stators located within said housing;
    b) a hub rotatably disposed within said housing, said hub having an axis of rotation and including a substantially hollow cavity arranged along said axis of rotation, said hub having a motor magnet located therewithin;
    c) a first permanent magnet bearing having inner and outer races and a second permanent magnet bearing having inner and outer races, each said permanent magnetic bearing located at an opposite extreme location along said axis of rotation, each said inner and outer races of each said first and second permanent magnet bearings are rings of permanent magnet material;
    d) an impeller disposed upon said hub within said flow path, said impeller being located axially between said motor magnet and at least one of said stator;
    e) an axial-gap, direct current, brushless motor formed by said stators and said motor magnet having a circumferential rotor and a circumferential stator;
    f) a sensor sensing an axial position of said hub; and
    g) a thrust coil for adjusting said axial position of said hub, said thrust coil being disposed toward an outside diameter of said axial-gap, direct current, brushless motor;
    wherein said first and second permanent magnet bearings passively, radially suspend said hub, said sensor controls activation of said thrust coil to maintain said axial position of said hub, and said axial-gap, direct current, brushless motor rotates said hub to provide fluid flow through said flow path via said impeller.

18. The pump as claimed in claim 17 wherein said thrust coil and said inner race of said second permanent magnet bearing form an active magnetic thrust bearing.

19. The pump as claimed in claim 17 wherein said hub further includes a magnet ring located at an outermost radial position on said hub, said thrust coil and said magnet ring forming an active magnetic thrust bearing.

20. The pump as claimed in claim 19 wherein said hub further includes ducts located between said first permanent magnet bearing and said impeller such that said flow path goes through said ducts.

* * * * *